United States Patent [19]

Mulligan-Kehoe

[11] Patent Number: 5,702,892
[45] Date of Patent: Dec. 30, 1997

[54] PHAGE-DISPLAY OF IMMUNOGLOBULIN HEAVY CHAIN LIBRARIES

[75] Inventor: Mary Jo Mulligan-Kehoe, Springfield, Va.

[73] Assignee: The United States of America as represented by the Department of Health and Human Services, Washington, D.C.

[21] Appl. No.: 437,815

[22] Filed: May 9, 1995

[51] Int. Cl.$^6$ .......................... C12Q 1/68; C12N 15/13; C12N 15/62; C12N 15/70

[52] U.S. Cl. .......................... 435/6; 435/69.1; 435/172.3; 435/320.1

[58] Field of Search .......................... 435/6, 172.3, 320.1, 435/69.1, 235.1

[56] References Cited

FOREIGN PATENT DOCUMENTS

| | | |
|---|---|---|
| 2276621 | 10/1994 | United Kingdom . |
| 92/18619 | 10/1992 | WIPO . |
| 94/18219 | 8/1994 | WIPO . |
| 94/18221 | 8/1994 | WIPO . |

OTHER PUBLICATIONS

Little et al., "Surface display of antibodies", Biotech. Adv. 12: 539–555, 1994.

Davies et al., "Antibody VH domains as small recognition units", Bio/Technol. 13: 475–479, May 4, 1995.

Barbas, C., et al. (1993) Direct selection of antibodies that coordinate metals from semisynthetic combinatorial libraries. Proc. Natl. Acad. Sci. 90:6385–6389.

Barbas, C., et al. (1992) Semisynthetic combinatorial anitbody libraries: a chemical solution to the diversity problem. Proc. Natl. Acad. Sci. 89:4457–4461.

Bradford, M. (1976) A rapid and sensitive method for the quantitation of microgram quantities of proteing utilizing the principle of protein–dye binding. Analytical Biochemistry 72:248–254.

Current Protocols in Molecular Biology. Ausbel et al. eds., Greene Publishing Associates and Wiley–Interscience (1987).

Deng, S., et al. (1993) Simultaneous randomization of antibody CDRs by a synthetic ligase chain reaction strategy. Nucleic Acids Research 21(18):4418–4419.

Holliger, P., et al. (1993) "Diabodies": small bivalent and bispecific antibody fragments. Proc. Natl. Adad. Sci. 90:6444–6448.

Hozumi, N., et al. (1993) Recombinant antibody technology: its advent and advances. Cancer Investigation 11(6):714–723.

Huse, W., et al. (1989) Generation of a large combinatorial librtary of the immunoglobulin repertoire in phage lambda. Science 246:1275–1281.

Kang, A., et al. (1991) Linkage of recognition and replication functions by assembling combinatorial antibody Fab libraries along phage surfaces. Proc. Natl. Acad. Sci. 88:4363–4366.

Kohler, G., et al. (1975) Continuous cultures of fused cells secreting antibody of predefined specificity. Nature 256:495–497.

Kohler, G., et al. (1976) Derivation of specific antibody–producing tissue culture and tumor lines by cell fusion. Eur. J. Immunol. 6:511–519.

Kozak, M. (1981) Possible role of flanking nucleotides in recognition of the AUG initiator codon by eukaryotic ribosomes. Nucleic Acids Research 9(20):5233–5252.

Methods of enzymatic analysis, vol. I; Bergmeyer et al. eds., Academic Press, Inc. (1974).

Molecular Cloning: A Laboratory Manual, Sambrook et al. eds., Cold Spring Harbor Lab Publ. (1989).

Mullinax, R., et al., (1990) Identification of human antibody fragment clones specific for tetanus toxoid in a bacteriophage ... Proc. Natl. Acad. Sci. 87:8095–8099.

Oldenberg, K., et al., (1992) Peptide ligands for a sugar–binding protein isolated from a random peptide library. Proc. Natl. Acad. Sci. 89:5393–5397.

Posner, B., et al., (1993) A revised strategy for cloning antibody gene fragments in bacteria. Gene 128:111–117.

Sharon, J. (1990) Structural correlated of high antibody affinity: three engineered amino acid substitutions can increase the affinity of an anti–p–azophenylarsonate andtibody 200–fold. Proc. Natl. Acad. Sci. 87:4814–4817.

Primary Examiner—Jasemine C. Chambers
Assistant Examiner—Scott D. Priebe
Attorney, Agent, or Firm—Knobbe, Martens, Olson & Bear, LLP

[57] ABSTRACT

One aspect of the invention relates to a phage-display library that expresses single-chain recombinant binding proteins. Inserts in the library comprise immunoglobulin heavy chain framework regions flanking highly divergent, synthetically produced hypervariable regions. A second aspect of the invention relates to the use of single-chain recombinant binding proteins to inhibit the activity of an intracellular constituent. In the exemplary case presented, the activity of intracellular glucose-6-phosphate dehydrogenase was inhibited by intracellular expression of a cloned single-chain recombinant binding protein.

4 Claims, 5 Drawing Sheets

PHAGE-DISPLAY OF IMMUNOGLOBULIN HEAVY CHAIN LIBRARIES

FIELD OF THE INVENTION

The present invention relates generally to the field of molecular immunology. More specifically, the invention relates to methods of using recombinant binding proteins to specifically bind and/or inhibit the activity of an intracellular constituent.

BACKGROUND OF THE INVENTION

The genes encoding immunoglobulin heavy and light chain proteins undergo rearrangements during B cell development to generate roughly $10^8$ different gene combinations. This diversity of gene structure directly contributes to the diversity of immunoglobulin binding specificity.

Hypervariable regions within the antigen binding pockets of immunoglobulins are responsible for the specificity of the interaction between an immunoglobulin and its target antigen. Both heavy and light chain variable regions harbor three hypervariable domains, also referred to as Complementarity Determining Regions (CDRs). The three CDRs are designated as CDRI-CDRIII, and are encoded by the recombined variable region gene segments.

The laboratory production of monoclonal antibodies advanced in 1975 with the introduction of hybridoma technology. The techniques of Kohler and Milstein (Nature 256:495 (1975); Eur. J. Immunol. 6:511 (1976)) enabled the production and purification of large amounts of a specific antibody. These techniques remained the preferred method of antibody production for nearly 15 years.

Antibody technology advanced again in 1988 with the discovery of a means for exploiting the potential of the mammalian immune system by identifying specific Fab fragments in combinatorial libraries. This technique, described by Huse et al. in Science 246:1275 (1988), utilized a biological system to create an immunoglobulin that bound an analog of a transition state intermediate of a reactant molecule with high affinity. A transition state intermediate is a chemical entity which represents the structure of the molecule as it transits from the reactant to the product form. Isolation of the immunoglobulin was accomplished by a procedure that involved stimulating a mouse to produce an immune response against a transition state analog. Spleen cell mRNA was then isolated and used as a template for reverse transcription and PCR amplification. These procedures ultimately led to the isolation of the heavy and light chain cDNAs which encoded the Fab fragment of an immunoglobulin that bound the transition state analog. Since the analog mimics the transition state intermediate along a chemical reaction pathway, the authors were able to utilize the isolated Fab fragment to influence the course of a reaction pathway. Indeed, the Fab fragment was demonstrated to have catalytic activity.

Herein we disclose another advance in the technology related to immunoglobulin-like proteins that specifically bind target antigens or ligands.

SUMMARY OF THE INVENTION

In a first aspect of the invention, there is provided a phage-display library. The library is constructed in an M13-derived expression vector and has, as an insert, a polynucleotide that spans the immunoglobulin heavy chain gene from a position upstream of complementarity determining region I (CDRI) to a position downstream of complementarity determining region III (CDRIII). The nucleotides encoding either CDRI or CDRIII comprise a plurality of synthetically produced random nucleotides. A fusion protein that includes amino acid sequences encoded by the vector insert is expressed on the outer surface of the recombinant phage which make up the library. The fusion protein can, for example, contain amino acids encoded by viral protein 8. Since these are phage display fusion protein constructs, this aspect of the invention constitutes a phage display library. The fusion proteins of the library are advantageously capable of binding a ligand.

A second aspect of the invention relates to a method of inhibiting an activity of an intracellular constituent. The intracellular constituent can, for example, be an enzyme. A first step in the method involves obtaining a phage-display library that expresses single-chain recombinant proteins having immunoglobulin heavy chain framework and hypervariable regions. The hypervariable regions of the library are encoded by a plurality of random nucleotides. A second step in the method involves screening the library to identify a phage clone that expresses a polypeptide able to bind a molecule that is an intracellular constituent. This screening can be conveniently carried out by first immobilizing the intracellular constituent to a solid support so that the specific phage(s) capable of binding to an immobilized support may be readily separated from phage that do not bind. The intracellular constituent advantageously has a biological activity that can be measured in an assay. Such an assay may be, for example, an enzymatic assay. The enzymatic assay may produce a reaction product that is a colored product. A third step in the method involves conducting an assay to verify that the biological activity of the intracellular constituent is inhibited in the presence of the polypeptide. A fourth step in the method involves purifying DNA from the phage clone that expresses a polypeptide able to bind a molecule that is an intracellular constituent. The purified DNA may be double-stranded if it is from a plasmid, or single-stranded if it is isolated from a phage clone. A PCR reaction can be carried out as part of the DNA isolation procedure. A fifth step in the method involves isolating a polynucleotide from the phage clone, where the isolated polynucleotide includes the framework and hypervariable regions, but not the secretion leader sequence. A sixth step in the method involves incorporating the polynucleotide into a eukaryotic expression vector to create a eukaryotic expression construct. The polynucleotide can conveniently be incorporated into the expression vector by a ligation reaction. Finally, the method involves inhibiting the activity of an intracellular constituent within a cell by introducing the eukaryotic expression construct into cells and allowing expression of the recombinant constituent binding polypeptide.

DETAILED DESCRIPTION OF THE INVENTION

Definition of Terms

Figure 1:
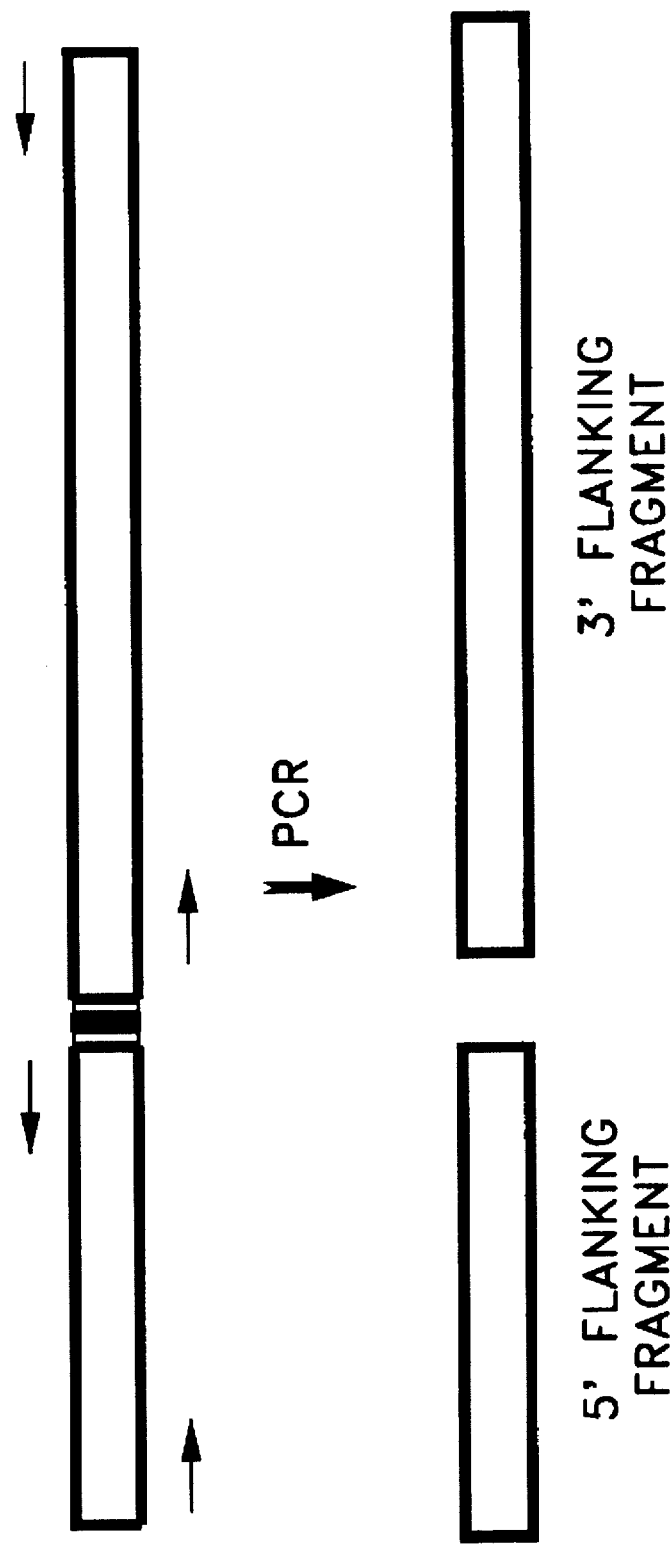
FIG. 1 schematically depicts a DNA template representing immunoglobulin heavy chain coding sequences and the binding sites of four oligonucleotide primers used to amplify regions flanking one of the CDRs.

As used herein, a "target" or "ligand" is a molecule that can bind a single-chain recombinant protein produced according to the invented method.

A "phage-display library" is a protein expression library, constructed in an M13-derived vector, that expresses a collection of cloned protein sequences as fusions with a phage coat protein. Thus, in the context of the invention, single-chain recombinant proteins having ligand-binding potential are expressed as fusion proteins on the exterior of the phage particle. This disposition advantageously allows contact and binding between the recombinant binding protein and an immobilized ligand. Those having ordinary skill in the art will recognize that phage clones expressing binding proteins specific for the ligand can be substantially enriched by serial rounds of phage binding to the immobilized ligand, dissociation from the immobilized ligand and amplification by growth in bacterial host cells.

"Framework" regions of the immunoglobulin heavy chain are those portions of the heavy chain variable region that are substantially conserved among heavy chains having different binding specificities.

Ligands for recombinant binding proteins produced according to the invented method can have measurable "biological activities." These activities include enzymatic activity, DNA binding activity, transcription factor activity, the ability to participate in subunit complex formation as would be relevant in signal transduction, and other activities that would be readily apparent to one having ordinary skill in the art.

"Eukaryotic expression vectors" are double-stranded DNA constructs that can direct the production of an mRNA when introduced into eukaryotic cells. The contemplated vectors carry cis-regulatory transcription factor binding sites that permit constitutive or inducible gene expression. The vectors can be plasmid vectors or viral vectors. Viral vectors include, among others, those based on vaccinia virus, adenovirus, adeno-related virus and herpes virus. Retroviral vectors, having single-stranded RNA genomes, are specifically contemplated for use with the invention, although the invention can be practiced with other expression vectors.

Introduction

We have discovered a method of engineering combinatorial libraries which differs from the conventional approach in that: 1) only heavy chain sequences are employed, 2) the heavy chain sequences are randomized at all nucleotide positions which encode either the CDRI or CDRIII hypervariable region, and 3) the genetic variability in the CDRs is generated independent of any biological process.

According to the invented method, two libraries were engineered to genetically shuffle oligonucleotide motifs within the framework of the heavy chain gene structure. Through random mutation of either CDRI or CDRIII, we reconstructed the hypervariable regions of the heavy chain gene to result in a collection of highly diverse sequences. The heavy chain proteins encoded by the collection of mutated gene sequences possessed the potential to have all of the binding characteristics of an immunoglobulin while requiring only one of the two immunoglobulin chains. Specifically, the present invention is practiced in the absence of the immunoglobulin light chain protein.

A phage expression library encoding recombinant proteins having heavy chain framework sequences and random hypervariable regions harbored clones that could bind and inhibit the activity of a target ligand. Structural modifications that included the addition of restriction enzyme recognition sites into the polynucleotide sequence encoding the recombinant binding proteins conveniently enabled genetic manipulation of the hypervariable gene sequences.

The re-engineered heavy chain gene sequences were ligated into an M13-derived bacteriophage cloning vector that permitted expression of a fusion protein on the phage surface. In the Examples presented below, the heavy chain protein sequences were expressed as fusion proteins with vital protein 8.

The method disclosed herein for selecting phage clones encoding recombinant proteins that bind a target ligand can be completed in a matter of hours. The procedure involves immobilizing a sample of a desired target ligand to a solid substrate. In the exemplary case presented below, the glucose-6-phosphate dehydrogenase (GPDH) protein served as a model ligand that was immobilized to magnetic beads by a streptavidin-biotin linkage.

Those having ordinary skill in the art will appreciate that the targets or ligands bound by the recombinant binding proteins of the present invention can be carbohydrates, lipids, proteins or nucleic acids. Further, these ligands can be either intracellular constituents or extracellular molecules. Intracellular constituents are represented by molecular species located within a cell. Such intracellular constituents can, for example, be enzymes, components of transmembrane signalling complexes, or transcription factors. Viral proteins are specifically contemplated as targets of the invention. A reverse transcriptase is one example of a viral protein contemplated as a target for binding and inhibition by the recombinant proteins of the present invention. Extracellular targets contemplated to fall within the scope of the invention include molecules that are present on the cell surface. Such surface-disposed molecules may, for example, be cell lineage-specific proteins or glycoproteins.

According to the invented method, a library of phage displaying modified heavy chain proteins is incubated with the immobilized ligand to select clones encoding recombinant proteins that specifically bind the immobilized ligand. The bound phage are then dissociated from the immobilized ligand and amplified by growth in bacterial host cells. Individual viral plaques, each expressing a different recombinant protein, are expanded to produce amounts of protein sufficient to perform an inhibition assay. In the Example presented below, a GPDH assay was performed to identify recombinant proteins that bound the GPDH protein and inhibited its enzymatic activity. Of 66 different recombinant phage clones that bound the immobilized GPDH enzyme, one plaque expressed a recombinant protein that inhibited 85% of the GPDH activity in an enzyme assay.

The DNA encoding this recombinant binding protein was subsequently modified for ligation into a eukaryotic protein expression vector. This modification entailed removal of the 5' secretion signal sequence and the addition of a translation initiation codon that directed translation of the recombinant binding protein. Stop codons were also incorporated into the construct in a region downstream of the coding sequence. All cloning procedures employed in the development of the invention were carried out according to standard laboratory practice. The mutant heavy chain gene, adapted for expression in eukaryotic cells, was ligated into a eukaryotic protein expression vector. For illustrative purposes, the expression vector used in the procedures detailed below harbored a promoter having lac response elements. The presence of these cis-regulatory elements enabled transcriptional induction by isopropyl thio-β-D- galactoside (IPTG).

Unless defined otherwise, all technical and scientific terms used herein have the same meaning as commonly understood by one having ordinary skill in the art to which this invention belongs. Although other materials and methods similar or equivalent to those described herein can be used in the practice or testing of the present invention, the preferred methods and materials are now described. General references for methods that can be used to perform the various PCR and cloning procedures described herein can be found in *Molecular Cloning: A Laboratory Manual* (Sambrook et al. eds. Cold Spring Harbor Lab Publ. 1989) and *Current Protocols in Molecular Biology* (Ausubel et al. eds., Greene Publishing Associates and Wiley-Interscience 1987). The disclosures of these references are hereby incorporated by reference.

Example 1 describes procedures used to isolate cDNA sequences that encoded a segment of an immunoglobulin heavy chain protein. The hybridoma cell line used as the source of RNA in this procedure secreted a monoclonal antibody having binding specificity for a hepatitis B antigen. While the invention has been carried out using the gene sequences encoding a particular heavy chain, other sources of RNA encoding heavy chains having other binding specificities could be used with equally good results. Those of ordinary skill in the art will appreciate that the source of starting RNA provides only the framework for the construction of nucleic acids that encode novel binding proteins.

EXAMPLE 1

Isolation and PCR Amplification of Heavy Chain cDNA Sequences

The H25B10 hybridoma cell line (ATCC, Rockville, Md.) was propagated in Dulbecco's modified Eagle's medium (DMEM) made 4.5 grams/liter glucose and 15% fetal bovine serum (FBS). RNA was isolated from the hybridoma cells by standard methods and then reverse transcribed to produce first strand cDNA using random primers and materials purchased as a kit from Boehringer-Mannheim (Indianapolis, Ind.).

The first-strand cDNA product was then used as the template in a PCR procedure to amplify a DNA fragment corresponding to a segment of the heavy chain cDNA. The amplification reaction included 50 pmol of a heavy chain 5' primer having the sequence, 5'-AGGTCCAGCTGCTCGAGTCAGG-3' (SEQ ID NO:1) and 50 pmol a heavy chain 3' primer having the sequence, 5'-AGGCTTACTAGTACAATCCCTGGGCACAAT-3' (SEQ ID NO:2). These oligonucleotides and the amplification protocol have been disclosed by Huse et al., in *Science* 246:1275 (1988).

The 0.6 kb amplification product was double-digested with XhoI and SpeI and ligated between the XhoI and SpeI sites of the pComb 8 vector to create the plasmid, pRuMu. Details regarding the pComb 8 vector have been presented by Kang et al., in *Proc. Natl. Acad. Sci.* 88:4363 (1991), the disclosure of which is hereby incorporated by reference. The ligation reaction was electroporated into *E. coli* strain XL1-Blue (Stratagene, La Jolla, Calif.) by standard methods. Transformed cells were selected by growth on LB/ampicillin (100 μg/ml) plates. A single bacterial colony containing the pRuMu plasmid was picked and grown in liquid culture medium containing 100 μg/ml ampicillin and 100 μg/ml tetracycline. When the culture density reached an $OD_{600}$ of 0.3, the lac z promoter was induced with 3 mM IPTG (Boehringer-Mannheim Corp., Indianapolis, Ind.). At one hour postinduction, helper phage M13K07 (Promega, Madison, Wis.) was added to the culture at a ratio of 10 phage: 1 bacterium. Kanamycin (Life Technologies, Inc., Gaithersburg, Md.) was added to a final concentration of 50 μg/ml at 90 minutes after helper phage addition. Shaking of the culture was continued at 37° C. for 5–12 hours.

Single stranded DNA (ssDNA) that was purified from the culture supernatant by standard methods served as a template in a dideoxy DNA sequencing protocol using SEQUE-NASE Version 2.0 purchased from United States Biochemical (Cleveland, Ohio). The DNA sequences corresponding to the CDRI and CDRIII regions of the heavy chain gene were identified in the cloned polynucleotide, as expected. The sequence of the cloned XhoI-SpeI heavy chain cDNA is presented as SEQ ID NO:3.

The procedures described in Example 1 enabled the isolation of a polynucleotide representing a segment of the heavy chain cDNA. The cloned fragment included sequences that spanned from a position upstream of CDRI to a position downstream of CDRIII. With the availability of this cloned fragment, it became possible to create recombinant binding proteins having novel binding specificities. This was accomplished by first engineering DNA fragments that flanked either CDRI or CDRIII of the heavy chain.

Example 2 describes the methods used to amplify nucleic acid sequences that flanked heavy chain CDRI and CDRIII regions. The DNA fragments upstream and downstream of CDRI are respectively referred to as the "5' fragment flanking CDRI" and the "3' fragment flanking CDRI." Similarly, the DNA fragments upstream and downstream of CDRIII are respectively referred to as the "5' fragment flanking CDRIII" and the "3' fragment flanking CDRIII."

EXAMPLE 2

Isolation of Gene Sequences Encoding Heavy Chain CDRI and CDRIII Flanking Regions DNA fragments flanking heavy chain CDRI and CDRIII were PCR amplified using the cloned heavy chain cDNA from Example 1 as a template and the following oligonucleotide primer sets and conditions:

---

5' fragment flanking CDRI:

CDRI 5' primer: 5' GGCCGCAAATTCTATTTCAAGGAG 3' (SEQ ID NO: 4)
CDRI 3' primer: 5' TGCCCTCAAGTTGCTTAAAGCC 3' (SEQ ID NO: 5)
3' fragment flanking CDR I:

5' primer: CACAGTGCACAGGG (SEQ ID NO: 6)
3' primer: 5' CGGCCGCTTAACTCTAGAACTGACGAGCTC 3' (SEQ ID NO: 7)

5' fragment flanking CDRIII:

5' primer: 5' GGCCGCAAATTCTATTTCAAGGAG 3' (SEQ ID NO: 4)
3' primer: 5' CCATGGAGGCCTGCATGCCTCAATGCACAT 3' (SEQ ID NO: 8)
3' fragment flanking CDRIII:

5' primer: 5' GCATGCAGGCCTCATATGACTCCTCACAACCC 3' (SEQ ID NO: 9)
3' primer: 5' CGGCCGCTTAACTCTAGAACTGACGAGCTC 3' (SEQ ID NO: 7)

Approximately 1 pg of plasmid pRuMu was combined with 50 pmol of the appropriate primer set defined above. Conditions employed in the PCR amplification of all flanking fragments were as follows: 95° C. for 10 minutes; 58° C. for 1 minute; add 1 µl Tac DNA polymerase (5 µl); 72° C. for 1.5 minutes followed by 34 cycles of: 95° for 1 minute; 58° C. for 1 minute; 72° C. for 1.5 minutes. FIG. 1 schematically depicts the locations of the primer binding sites relevant to the amplification of the 5' fragment and the 3' fragment flanking one of the two CDRs. Significantly, primers having the sequences of SEQ ID NO:4 and SEQ ID NO:7 had binding sites in vector sequences and not in the heavy chain coding sequences presented as SEQ ID NO:3.

Sizes of the amplified DNA fragments were determined by agarose gel electrophoresis and staining with ethidium bromide. The 5' and 3' fragments flanking CDRI had lengths of approximately 0.23 and 0.77 kb, respectively. The 5' and 3' fragments flanking CDRIII had lengths of approximately 0.55 and 0.57 kb, respectively.

The flanking DNA fragments amplified as in the preceding Example served as templates for the introduction of DNA sequence variability into the CDRI and CDRIII regions. More specifically, the following Example illustrates the method used to create a collection of polynucleotides in which the CDRI or CDRIII regions of the heavy chain variable region comprise a span of random nucleotides.

Example 3 describes the protocol used to create a collection of polynucleotides harboring a stretch of random nucleotides bordered by CDRI or CDRIII flanking sequences.

EXAMPLE 3

Introducing Genetic Variation into Sequences Corresponding to Heavy Chain CDRI and CDRIII Two different oligonucleotides comprising randomly mutated CDRI or CDRIII regions were prepared on an Applied Biosystems 394 DNA synthesizer. The sequences of these oligonucleotides were chosen such that the nucleotides flanking the centrally disposed random nucleotide inserts could hybridize the 3' end of the 5' fragment flanking the CDR while simultaneously hybridizing the 5' end of the 3' fragment flanking the CDR. Both of the flanking fragments used in the procedure were prepared as described in Example 2. The sequence at the 5' and 3' ends of CDRI had unique restriction sites. Therefore, all 39 of the intervening nucleotides between the MnlI and ApaII restriction sites which bordered CDRI were random in the CDRI library. To facilitate subsequent cloning procedures in the CDRIII library, restriction enzyme recognition sequences were incorporated into the CDRIII oligonucleotide. The structures of the CDRI and CDRIII oligonucleotides employed in these procedures are presented below.

The CDRI oligonucleotide had the sequence:
5' GGCTTTAAGCAACTTGAGGGCA---39 random nucleotides---CACAGTGCACAGGG-3' (SEQ ID NO:10).

The CDRIII oligonucleotide had the sequence:
5'-TATGTGCATTGAGTCGATGC---15 random nucleotides---CATATGACTCCTCACAACCC-3' (SEQ ID NO:11).

Figure 2:
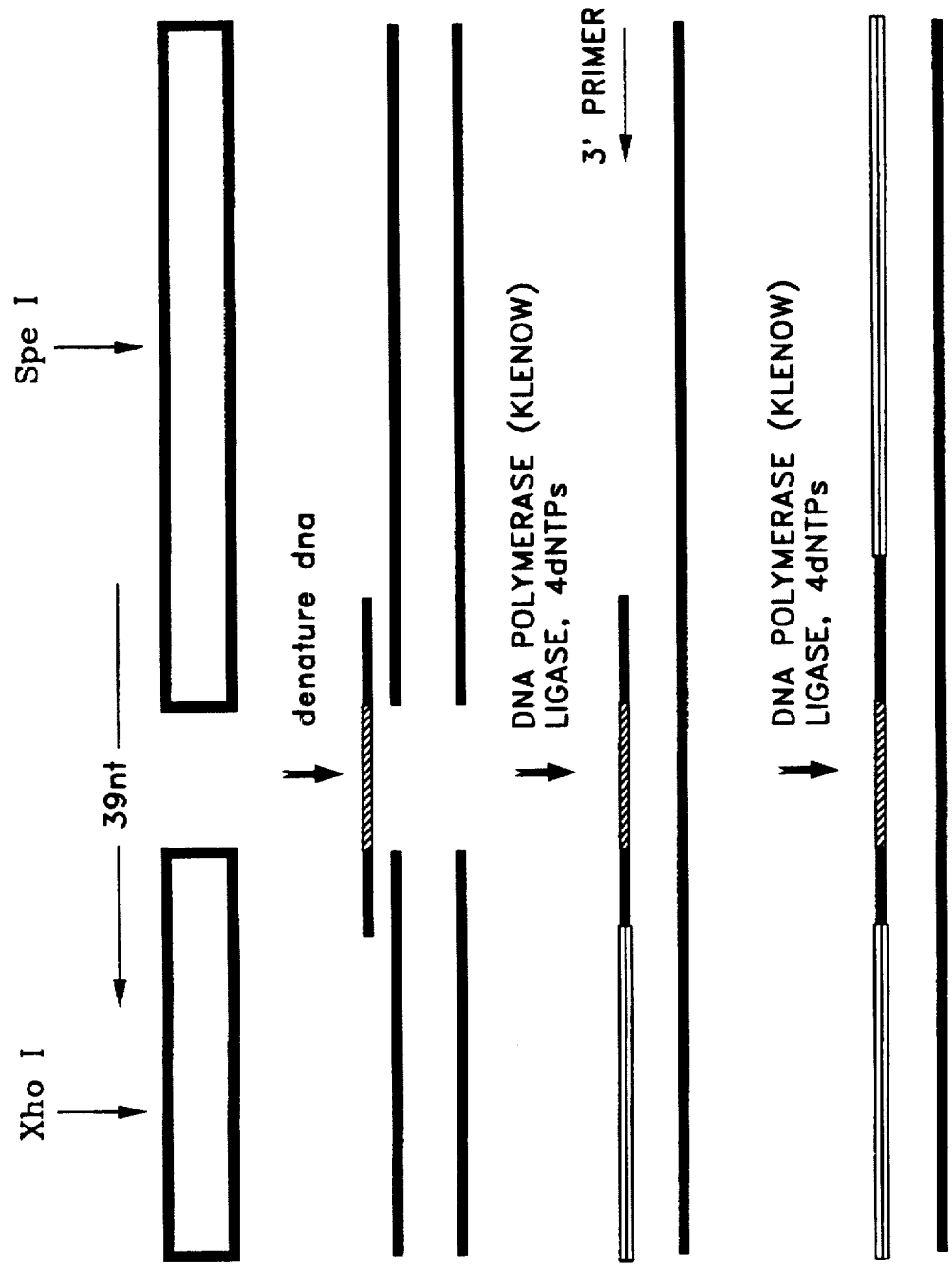
FIG. 2 schematically depicts the method for incorporating a synthetic CDRI oligonucleotide into the structure of the heavy chain coding sequence.
Figure 3:
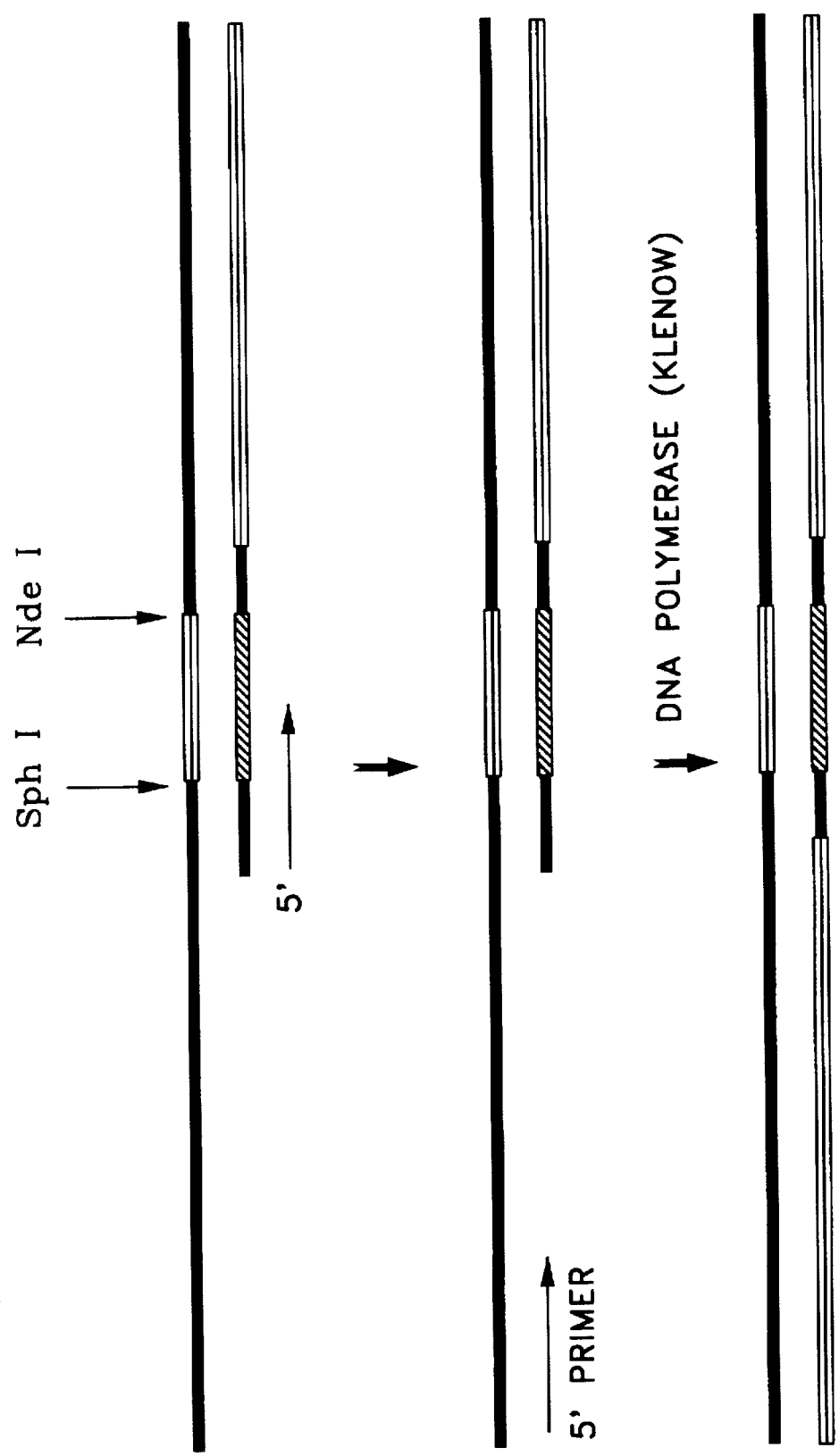
FIG. 3 schematically depicts the method for incorporating a synthetic CDRIII oligonucleotide into the structure of the heavy chain coding sequence.

The CDRI or CDRIII oligonucleotides were separately incorporated into the heavy chain flanking fragments and made double stranded by the activity of the Klenow fragment of DNA polymerase I. The binding, extension and ligation of primers having binding sites on the 5' and 3' fragments that flanked the CDRs are schematically depicted in FIG. 2 (CDRI) and FIG. 3 (CDRIII). The method for amplifying the flanking fragments that served as DNA templates in this reaction is presented in Example 2. The DNA molecule harboring the random CDRI oligonucleotide was made fully double-stranded by performing a second polymerization reaction using a short 3' primer, additional Klenow polymerase, dNTPs and ligase. The 3' primer had the sequence, 5'-GAACTGACGAGCTCGGCCATGGCT-3' (SEQ ID NO:12). The position of the 3' primer binding site and the procedure used to accomplish this reaction is schematically depicted in FIG. 2. The DNA molecule harboring the random CRDIII oligonucleotide was similarly made double-stranded by performing a second polymerization reaction using a short 5' primer, additional Klenow polymerase, dNTPs and ligase. The standard procedures employed to carry out the Klenow polymerization reaction are generally disclosed in *Molecular Cloning: A Laboratory Manual* (Sambrook et al. eds. Cold Spring Harbor Lab Publ. 1989).

The procedure for incorporating the CDRI oligonucleotide (SEQ ID NO:10) into a double stranded DNA molecule having a heavy chain scaffold was carried out as follows. The reaction included the following components: 2.5 pmol of each of the two fragments that flank CDRI, 10.0 pmol of mutated CDRI oligonucleotide and buffer PE1 (20 mMTris HCl (pH 7.5), 10 mM MgCl$_2$, 50 mM NaCl, 1 mM dithiothreitol). The mixture was incubated at 95° C. for 5 minutes; 68° C. for 2 minutes; and then brought to room temperature for 20 minutes. Following this denaturing/annealing step, the randomly mutated hypervariable region was made double stranded by the activities of Klenow polymerase and T4 ligase.

Verification of the completed reaction was accomplished by a PCR probing protocol that involved amplifying DNA fragments between the NotI and XbaI sites of the vector which would flank the inserts in the CDRI library. The PCR reaction mixture included 50 pmol each of primers having the sequence of SEQ ID NO:4 and SEQ ID NO:7, and a 1 µl sample of the complete double-stranded DNA molecule containing the mutated CDRI region within the heavy chain scaffold that resulted from the second klenow polymerization reaction following addition of the primer having the sequence of SEQ ID NO:12. The amplification of a fragment of approximately 1 kb using primers having the sequences of SEQ ID NO:4 and SEQ ID NO:7, and amplification of a 0.6 kb fragment using primers having the sequences of SEQ ID NO:1 and SEQ ID NO:2 confirmed the construction of DNA molecules having the structure represented as the product in FIG. 2.

A similar procedure was followed to create a collection of double stranded DNA molecules incorporating randomly mutated CDRIII oligonucleotides. This reaction included each of each of the two DNA fragments flanking CDRIII, the collection of mutated CDRIII oligonucleotides (SEQ ID NO:11) and a primer having the sequence 5'-GGCCGCAAATTCTATTTCAAGGAG-3' (SEQ ID NO:4).

The re-engineered heavy chain genes harboring either a mutated CDRI or mutated CDRIII region were digested with XhoI and SpeI and ligated between the XhoI and SpeI sites of the pComb 8 vector.

E. coli XL1-Blue cells were transformed with a 4 µl sample of the ligation reaction by electroporation according to standard laboratory methods. Immediately after electroporation, the transformation mixture was combined with 1 ml of super broth and incubated at 37° C. for 1 hour. The entire volume of the transformation mixture was plated on LB/ampicillin plates. All bacterial growth was washed from the plate and transferred to super broth containing 100 µg/ml ampicillin and 100 µg/ml tetracycline until the culture density reached an $OD_{600}$ of 0.3. Thereafter the growth conditions, promoter induction and addition of helper virus were as described in Example 1. A sample of the library was titered on E. coli XL1-Blue host cells. The CDRI library had a titer of $6 \times 10^{10}$ pfu/ml, while the CDRIII library had a titer of $2 \times 10^{12}$ pfu/ml.

Example 4 describes the methods used to identify recombinant phage that expressed an engineered heavy chain protein which bound a target ligand with high affinity. In this Example, GPDH served as the target ligand for which a binding protein was sought.

EXAMPLE 4

Library Screening

The CDRI phage library was concentrated by incubating the culture supernatant with 20% polyethylene glycol 8000 and 3.4M NaCl at room temperature for 30 minutes with stirring. Precipitated phage were pelleted by centrifugation for 45 minutes, 15,000 rpm, 4° C. in a Beckman SW28 rotor. The phage pellet was resuspended in 1 ml PBS (pH 7.5).

Sulfosuccinimidyl-6-(biotinamido) hexanoate (Pierce, Rockford, Ill.) was conjugated to GPDH (Sigma, St. Louis, Mo.) according to the manufacturer's protocol. Unreacted biotin was removed using a centricon-30 microconcentrator (Amicon, Inc., Beverly, Mass). Biotin incorporation was determined by measuring (absorption at 500 nm) displacement of free biotin from HABA dye (2-(4'-hydroxyazobenzene)-benzoic acid) (Pierce, Rockford, Ill.) when incubated with sulfosuccinimidyl-6-(biotamido) hexanoate conjugated GPDH.

Dynabeads M-280 Streptavidin magnetic beads (Dynal, Lake Success, N.Y.) were washed, and incubated with biotinylated GPDH for 1 hour at room temperature with mild agitation to promote binding. The beads were then washed 3 times with PBS made 0.1% TWEEN-20, and followed by 3 washes with PBS to remove free biotinylated GPDH. The streptavidin-coupled dynabeads having bound biotinylated GPDH were incubated with 1 ml of concentrated library phage for 2 hours at room temperature with gentle agitation. Following the incubation, the bound phage were removed from the mixture as stepped fractions by application of a magnet to the container holding the bead/phage mixture. The bead-immobilized phage were dissociated from the beads by first incubating the bead/phage mixture at 65° C. Phage released from the beads were collected in the supernatant. Phage that remained bound to the beads following the 65° C. incubation were next dissociated from the beads by incubating the bead/phage mixture in 50 µl 0.5M citric acid (pH 5), for 10 minutes at room temperature. Phage released from the beads were again collected in the supernatant and the pH of the sample raised to 7.0 by addition of 1 ml PBS (pH 7.5). The most stringently bound phage were dissociated from the bead-immobilized GPDH by incubation in 50 µl 0.1N HCl buffer (pH 2.2), at room temperature for 10 minutes. Once the beads were separated from the incubation mixture, the pH of the sample was neutralized by addition of 6 µl of 1M Tris base that was not pH-adjusted.

Phage collected at each step of the dissociation procedure were used to infect E. coli XL1-blue cells in super broth containing 100 µg/ml of tetracycline. Cultures were grown overnight at 37° C., with shaking. The supernatant containing recombinant phage was collected and concentrated as described. Resuspended phage were once again incubated with biotinylated GPDH immobilized to streptavidin-coupled magnetic beads. Dissociation of phage bound to GPDH was repeated as described. The selection procedure, comprising cycles of phage growth/phage binding to GPDH/phage release, was repeated a third time.

Individual plaques representing clones isolated from the third cycle of selection were picked and incubated with E. coli XL1-blue cells and grown in broth made 100 µg/ml tetracycline. The lac promoter was induced, and both helper virus and kanamycin were added as described above. Phage were isolated from the supernatant and concentrated by standard methods. The cloned phage expressed recombinant fusion proteins that specifically bound GPDH.

Example 5 describes the procedures used to test the ability of a recombinant heavy chain protein to inhibit the activity of the target ligand. In this exemplary demonstration, a GPDH assay was performed to identify a recombinant phage expressing GPDH binding protein.

EXAMPLE 5

Assay to Confirm Inhibitory Activity of the Recombinant Heavy Chain Protein

Sixty-six clonal phage isolates were chosen for the ability to bind the GPDH ligand according to the method of Example 4. Equivalent amounts of each phage sample were then aliquotted by estimating that protein and phage concentrations were proportional to each other. Protein concentrations were determined by the Bradford assay (Anal. Biochem. 72:248 (1976)). Samples (1 µg protein) were incubated at room temperature with 1 unit of GPDH, and bovine serum albumin at a concentration equivalent to sample protein. At various time intervals, 0.02 ml samples of the incubation mixture were added to 2.5 ml of 0.1M triethanolamine buffer (pH 7.6), 0.2 ml of 0.1M $MgCl_2$, 0.1 ml glucose-6-phosphate, sodium salt (10 mg/ml), 0.1 ml NADP, sodium salt (10 mg/ml). Glucose-6-phosphate dehydrogenase activity was measured at a wavelength of 340 nm according to the method of Bergmeyer et al. as disclosed in Methods of Enzymatic Analysis 1:458 (1974). A sample that did not contain the recombinant binding protein served as a positive control in the assay.

Figure 4:
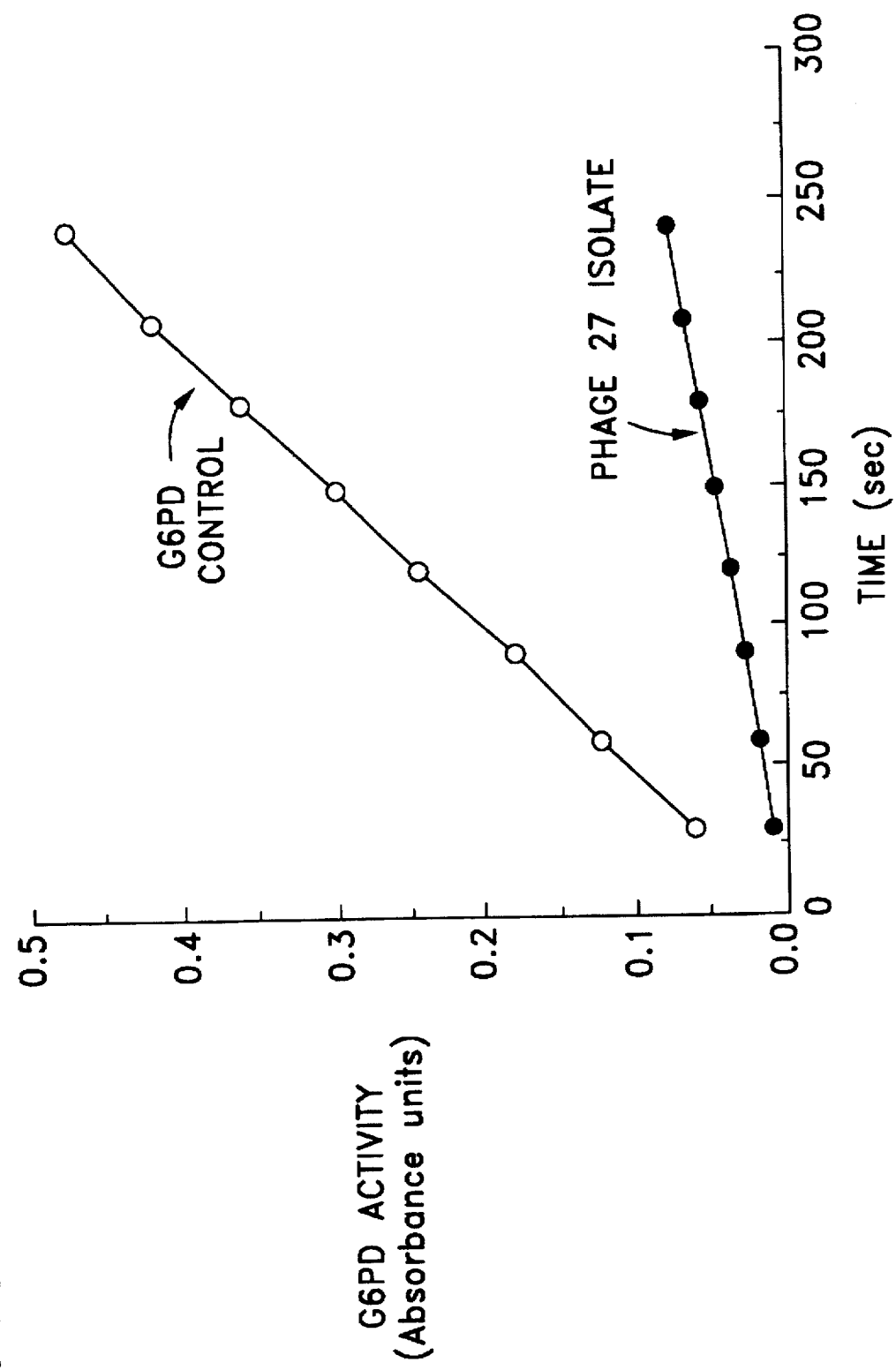
FIG. 4 presents graphic results demonstrating that a phage clone (D27) can inhibit glucose-6-phosphate dehydrogenase activity in an enzymatic assay.

Results of this assay, presented in FIG. 4, confirmed that the phage isolate D27 strongly inhibited GPDH activity. Comparison of the slopes of the two lines in the figure indicated that the recombinant protein encoded by phage D27 inhibited 85% of the GPDH activity in the assay.

The preceding results proved that a recombinant phage library expressing engineered heavy chain proteins, in which CDRI or CDRIII were replaced by random nucleotides, can be used to produce and select novel proteins that bind a target ligand with high affinity. In the exemplary case presented above, an engineered heavy chain protein was selected by a procedure that involved binding of the target ligand (GPDH) to phage that displayed a recombinant ligand binding protein.

The invented method advantageously introduces enormous genetic variation into the hypervariable regions of an immunoglobulin heavy chain fragment. The variability results from the fact that the nucleotides encoding the amino acids of CDRI and CRDIII of a rearranged heavy chain gene have been substituted by random nucleotides.

Those having ordinary skill in the art will readily appreciate that more than one round of mutagenesis and selection can be performed to perfect or mature the binding properties of recombinant binding proteins produced according to the invented method. More particularly, we contemplate a process wherein a first library of phage harboring recombinant heavy chain gene sequences mutant in one CDR (eg. CDRI) is screened to identify a first clone that encodes and expresses a protein having desirable ligand binding properties. The DNA of the first clone can then serve as a starting material for the creation of a second library of phage harboring recombinant heavy chain gene sequences mutant in a different CDR (eg. CDRIII). Accordingly, CDRI and CDRIII can be sequentially mutated to result in a construct that encodes a single protein, mutated in both CDRI and CDRIII, having optimal ligand binding properties.

The results presented below illustrate how intracellular expression of recombinant heavy chains produced in accordance with the invented method can inhibit the activity of intracellular protein targets. The DNA encoding the recombinant heavy chain was first adapted to permit intracellular expression in eukaryotic cells. The adaptation procedure will typically entail deletion of the secretion signal sequence, addition of a 5' initiation codon and a stop codon at the 3' end of the nucleic acid sequence to be expressed as mRNA encoding the recombinant binding protein.

Example 6 describes a process for adapting gene sequences which encode recombinant binding proteins to intracellular expression in eukaryotic cells.

EXAMPLE 6

Intracellular Expression of Recombinant Heavy Chain Protein

The DNA from phage DH27 was isolated using a Qiagen Maxi plasmid purification kit (Qiagen, Inc., Chatsworth, Calif.). Alteration of the DH27 heavy chain DNA was accomplished using a PCR protocol that employed the DH27 DNA template and two PCR primers. The 5' terminus of the 5' primer used in the following procedure included a NOT I restriction enzyme recognition sequence that was followed by a Kozak translation initiation motif (*Nucleic Acid Res.* 9:5233 (1981)), an ATG translation initiation codon, and an additional 15 nucleotides located downstream of the ATG codon. The downstream region of the 5' primer sequence was complimentary to an upstream region of the gene sequence that encoded the GPDH specific binding protein. The 3' oligonucleotide was designed to introduce three stop codons and a NOTI site into the amplified product.

5' PRIMER: 5'-GCGGCCGCGCCGCCACCATGCATTTGGACTTCTGG-3' (SEQ ID NO: 13)
3' PRIMER: 5'-GCGGCCGCTTATCATCAACTAGTACAATCCCTGGGC-3' (SEQ ID NO: 14)

PCR conditions were as follows: a total reaction volume of 100 μl contained 50 pmol of each of the 5' and 3' primers, 200 pg of phage DNA, and 10 μl of a 10× reaction buffer containing: 20 mM Tris-HCl (pH 8.0), 1 mM DTT, 0.1 mM EDTA, 0.01M KCl, NONIDET P40 (0.5% v/v), TWEEN 20 (0.5% v/v) and 20% glycerol. The mixture was denatured at 95° C. for 1 minute, annealed at 58° C for 1.5 minutes followed by elongation at 72° C. for 1 minute. These conditions were repeated for 35 rounds to yield an amplification product of 0.55 kb. The re-engineered DH27 heavy chain (DH27/805) amplification product was digested with NOTI and ligated into the NotI site of the pOPRSV1 eukaryotic protein expression vector (Stratagene, La Jolla, Calif.). Conventional procedures were then used to identify a clone having an insert orientation such that induction of the vector-borne promoter led to production of an mRNA that could be translated into recombinant heavy chain protein that bound GPDH. The plasmid containing DH27/805 heavy chain coding sequence and vector p3'ss were co-electroporated into V79 cells. The conditions for electropoation were as follows: 4×10$^6$ cells/400 μl of 10 mM HEPES buffer, 15 μg of each vector (linear) in a 0.4 cm cuvette were pulsed with 0.25 kV, 960 uF. Electroporated cells were immediately transferred to 5 ml of F12 growth medium supplemented with 10% FCS and incubated at 37° C. Approximately 36 hours after electroporation, at a time when cell attachment was apparent, 400 μg/ml G418 and 400 μg/ml of hygromycin were added to the medium to select for cells harboring pORSV1/DH27/805 and p3'ss respectively.

Figure 5:
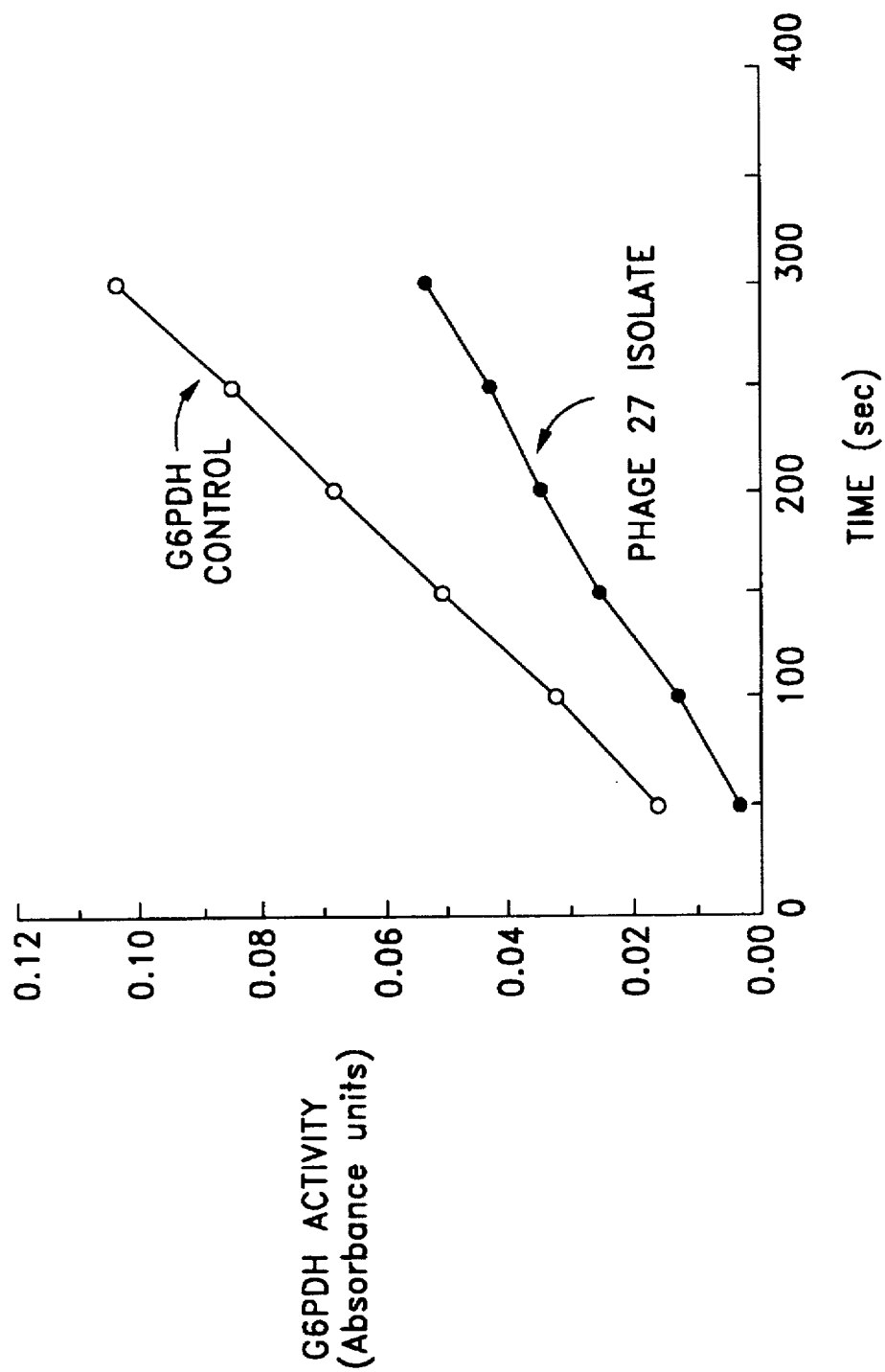
FIG. 5 presents graphic results demonstrating that an intracellularly expressed single-chain recombinant binding protein inhibited the activity of an intracellular enzyme.

150 mM dishes were seeded with 3×10$^6$ V79 cells containing pOPRSV1/DH27/805 and p3'ss 10 hours prior to induction of the promoter with either 5 mM or 10 mM IPTG or no induction. Cells were harvested from the plates at 15 hours following promoter induction. Glucose-6-phosphate dehydrogenase activity was measured in a sample of cellular extract containing 50 μg of total cellular protein. Results from the assay are presented in FIG. 5.

We have described a method of making and using a phage-display library that encodes a highly diverse collection of single-chain recombinant binding proteins. The recombinant proteins are encoded by polynucleotides comprising segments corresponding to immunoglobulin heavy chain framework regions that flank synthetically produced hypervariable regions. The phage library was screened to identify clones encoding proteins that bound a ligand of choice. An intracellular enzyme, glucose-6-phosphate dehydrogenase, was selected to illustrate the operation of the invention. The cloned ligand-specific proteins were then tested for their ability to inhibit enzymatic activity of glucose-6-phosphate dehydrogenase using no more than routine experimentation. The polynucleotide encoding the recombinant binding protein was then transferred to a eukaryotic expression vector, and the resulting construct introduced into living cells. The activity of intracellular glucose-6-phosphate dehydrogenase was inhibited by intracellular expression of the recombinant single-chain binding protein having specificity for the enzyme.

What is claimed is:

1. A phage-display library, comprising:
   a plurality of recombinant phage, each of said recombinant phage including an M13-derived expression vector having incorporated therein a polynucleotide coding for a polypeptide a protein encompassing a region spanning from upstream of an immunoglobulin heavy chain CDRI to a position downstream of CDRIII, wherein a DNA sequence encoding either CDRI or CDRIII is replaced by a randomly ordered DNA sequence, and wherein a fusion protein comprising the polypeptide encoded by said polynucleotide is expressed in the absence of an immunoglobulin light chain protein or portions thereof on an outer surface of recombinant phage of the library.

2. The phage-display library of claim 1, wherein the fusion protein is a fusion with viral protein 8.

3. A phage display library comprising a plurality of recombinant phage, each of said recombinant phage including an M13-derived expression vector having incorporated therein a polynucleotide coding for a polypeptide encompassing a region spanning from upstream of an immunoglobulin heavy chain CDRI to a position downstream of CDRIII, wherein a DNA sequences encoding CDRI and CDRIII are each replaced by randomly ordered DNA sequences, and wherein a fusion protein comprising the polypeptide encoded by said polynucleotide is expressed in the absence of an immunoglobulin light chain polypeptide or portions thereof on an outer surface of recombinant phage of the library.

4. An isolated phage clone comprising:
   an M13-derived expression vector having incorporated therein a polynucleotide coding for a polypeptide encompassing a region spanning from upstream of an immunoglobulin heavy chain CDRI to a position downstream of CDRIII, wherein a DNA sequence encoding CDRI or a DNA sequence encoding CDRIII is replaced by a randomly ordered DNA sequence, and wherein a fusion protein comprising the polypeptide encoded by said polynucleotide is expressed in the absence of an immunoglobulin light chain polypeptide or portions thereof on an outer surface of the phage clone.

* * * * *

UNITED STATES PATENT AND TRADEMARK OFFICE
CERTIFICATE OF CORRECTION

PATENT NO.     : 5,702,892
DATED          : December 30, 1997
INVENTOR(S)    : Mary Mulligan-Kehoe It is certified that error appears in the above-identified patent and that said Letters Patent is hereby corrected as shown below:

Column 21,
Line 49, delete "protein" and insert -- polypeptide --.

Column 22,
Line 48, delete "CDRI1I" and insert -- CDRIII --.

Signed and Sealed this

Thirtieth Day of September, 2003

JAMES E. ROGAN
*Director of the United States Patent and Trademark Office*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
       ( A ) LENGTH: 22 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

AGGTCCAGCT GCTCGAGTCA GG 22

( 2 ) INFORMATION FOR SEQ ID NO:2:

( i ) SEQUENCE CHARACTERISTICS:
       ( A ) LENGTH: 30 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:2:

AGGCTTACTA GTACAATCCC TGGGCACAAT 30

( 2 ) INFORMATION FOR SEQ ID NO:3:

( i ) SEQUENCE CHARACTERISTICS:
       ( A ) LENGTH: 612 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
       ( A ) NAME/KEY: Other
       ( B ) LOCATION: 137...175
       ( D ) OTHER INFORMATION: CDRI coding region
       ( A ) NAME/KEY: Other
       ( B ) LOCATION: 444...476
       ( D ) OTHER INFORMATION: CDRIII coding region ( x i ) SEQUENCE DESCRIPTION: SEQ ID NO:3:

| | | | | | |
|---|---|---|---|---|---|
| CTCGAGTCAG | GGGGAATGGA | AGGGAGTCTC | CAGATCTCAG | TCAGCTAGCA | GTTTAGATCC | 60 |
| TTAGGTGGAA | TCTCTTATGA | GCTGATGCAT | TTGGACTTCT | GGCCCAGGCT | TTAAGCAACT | 120 |
| TGAGGGCAGA | GATACTGTAA | TTCTTATTTG | GTTCTTGCCA | TCTGGCACAC | AGTGCACAGG | 180 |
| GTTATACACT | CAGTGAATGC | TGAATGAGTG | AAGGAGCTGA | ATTCCTTCAT | TTCTCAAGTT | 240 |
| CTCATTTCTT | CACTCAACAA | ACATTCATTG | ACCTTCACTT | TGTGCCAGGC | CCTAAGCTAG | 300 |
| AGGCTGGGGG | TTGGGGAAGG | GACAGAAAGA | CAAGTTAACA | ACCTGAGCTA | TGAGCTGCCC | 360 |
| CTGCGGAGAT | TCATGCCAGT | CTGGGATCCA | TTGTAACAAT | GGCTGCCATT | GGTTGCAGGT | 420 |
| CTACTATGTG | CATTGAGTCA | AGCATTTGG | ACAAATGATC | TTGTTACTC | CTCACAACCC | 480 |
| TAGGAGATAC | TATTATCATC | CCATTTATA | GATGATGACA | CTGAGGCTTA | GAAAGGTTGG | 540 |
| TTAAGACACA | CTTTCCAAGG | CATACAGCTA | GTGTGTGGTA | GATCCAAGAT | TGTGCCCAGG | 600 |
| GATTGTACTA | GT | | | | | 612 |

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:4:

GGCCGCAAAT TCTATTTCAA GGAG    24

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:5:

TGCCCTCAAG TTGCTTAAAG CC    22

( 2 ) INFORMATION FOR SEQ ID NO:6:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

CACAGTGCAC AGGG     14

(2) INFORMATION FOR SEQ ID NO:7:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

CGGCCGCTTA ACTCTAGAAC TGACGAGCTC     30

(2) INFORMATION FOR SEQ ID NO:8:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

CCATGGAGGC CTGCATGCCT CAATGCACAT     30

(2) INFORMATION FOR SEQ ID NO:9:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

```
GCATGCAGGC CTCATATGAC TCCTCACAAC CC                                              32
```

( 2 ) INFORMATION FOR SEQ ID NO:10:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:10:

```
GGCTTTAAGC AACTTGAGGG CANNNNNNNN NNNNNNNNNN NNNNNNNNNN NNNNNNNNNN               60
NCACAGTGCA CAGGG                                                                75
```

( 2 ) INFORMATION FOR SEQ ID NO:11:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:11:

```
TATGTGCATT GAGTCGATGC NNNNNNNNNN NNNNNCATAT GACTCCTCAC AACCC                    55
```

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:12:

```
GAACTGACGA GCTCGGCCAT GGCT                                                      24
```

( 2 ) INFORMATION FOR SEQ ID NO:13:

( i ) SEQUENCE CHARACTERISTICS:
        ( A ) LENGTH: 35 base pairs
        ( B ) TYPE: nucleic acid
        ( C ) STRANDEDNESS: single ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:13:

GCGGCCGCGC CGCCACCATG CATTTGGACT TCTGG      35

( 2 ) INFORMATION FOR SEQ ID NO:14:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:14:

GCGGCCGCTT ATCATCAACT AGTACAATCC CTGGGC      36